(12) United States Patent  (10) Patent No.: US 8,043,298 B2
Capanni  (45) Date of Patent: Oct. 25, 2011

(54) TOOL SYSTEM FOR ADAPTING A BONE PLATE

(75) Inventor: Felix Capanni, Freiburg (DE)

(73) Assignee: Stryker Leibinger GmbH & Co., KG, Freiburg (DE)

( * ) Notice: Subject to any disclaimer, the term of this patent is extended or adjusted under 35 U.S.C. 154(b) by 1187 days.

(21) Appl. No.: 11/742,348

(22) Filed: Apr. 30, 2007

(65) Prior Publication Data

US 2007/0213713 A1    Sep. 13, 2007

Related U.S. Application Data

(62) Division of application No. 10/446,972, filed on May 28, 2003, now Pat. No. 7,229,446.

(30) Foreign Application Priority Data

May 29, 2002    (DE) .................................. 102 24 005

(51) Int. Cl.
 *A61B 17/58* (2006.01)
 *A61B 17/60* (2006.01)
 *A61F 2/00* (2006.01)
(52) U.S. Cl. ....................................................... 606/101
(58) Field of Classification Search ................ 606/86 R, 606/101; 7/132
 See application file for complete search history.

(56) References Cited

U.S. PATENT DOCUMENTS

| | | | |
|---|---|---|---|
| 1,912,763 A | | 6/1933 | Crossgrove |
| 2,737,835 A | | 3/1956 | Herz |
| 3,507,284 A | | 4/1970 | Simmons et al. |
| 3,796,201 A | * | 3/1974 | Golub ................................ 140/1 |
| 3,857,389 A | | 12/1974 | Amstutz |
| 3,872,898 A | * | 3/1975 | Parks ............................ 140/105 |
| 4,033,388 A | * | 7/1977 | Ruegger ......................... 140/106 |
| 4,571,764 A | * | 2/1986 | Chen et al. ......................... 7/107 |
| 4,610,279 A | * | 9/1986 | Stewart ........................... 140/105 |
| 5,306,319 A | | 4/1994 | Krishnan et al. |
| 5,957,927 A | | 9/1999 | Magee et al. |
| 6,077,271 A | | 6/2000 | Huebner et al. |
| 2003/0187441 A1 | | 10/2003 | Bolger et al. |
| 2004/0116934 A1 | | 6/2004 | Capanni |

* cited by examiner

*Primary Examiner* — Thomas C. Barrett
*Assistant Examiner* — David Bates
(74) *Attorney, Agent, or Firm* — Howard & Howard Attorneys PLLC

(57) ABSTRACT

A tool system for working on a bone plate is described. The tool system includes a first tool and a second tool, used at the same time as the first tool to shorten or bend the bone plate. Each of the two tools includes one or more introduction openings with which in turn one or more blades may be associated.

14 Claims, 5 Drawing Sheets

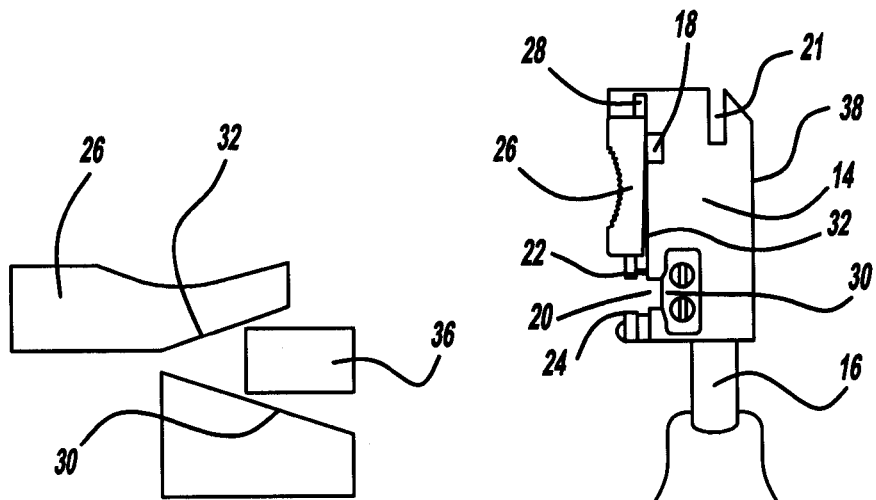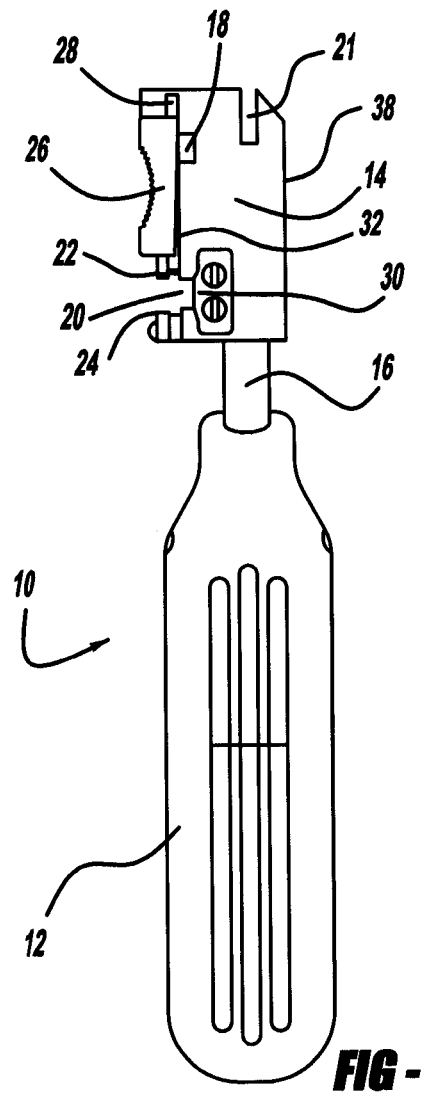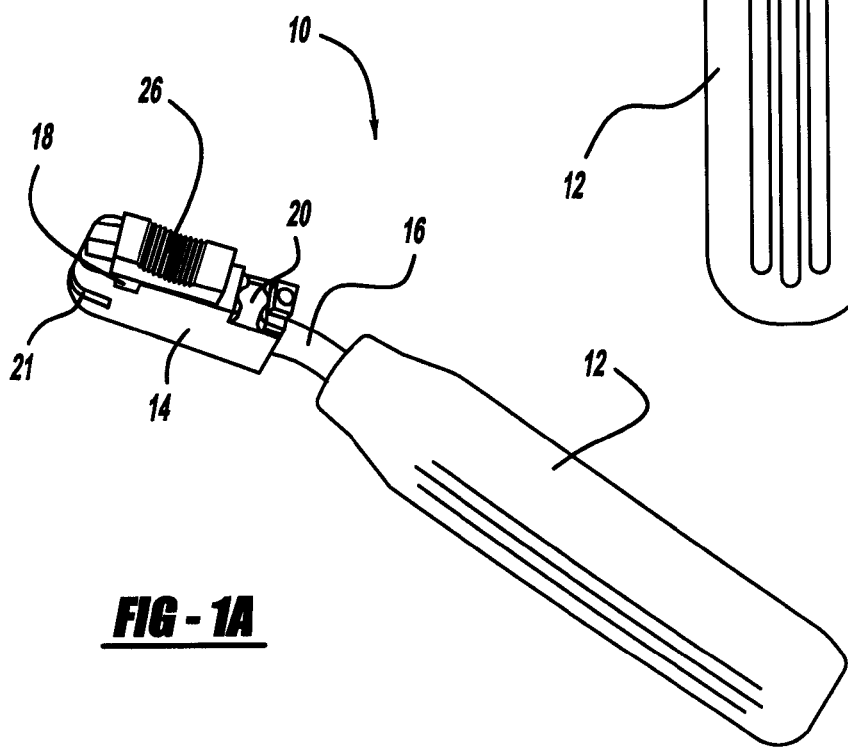

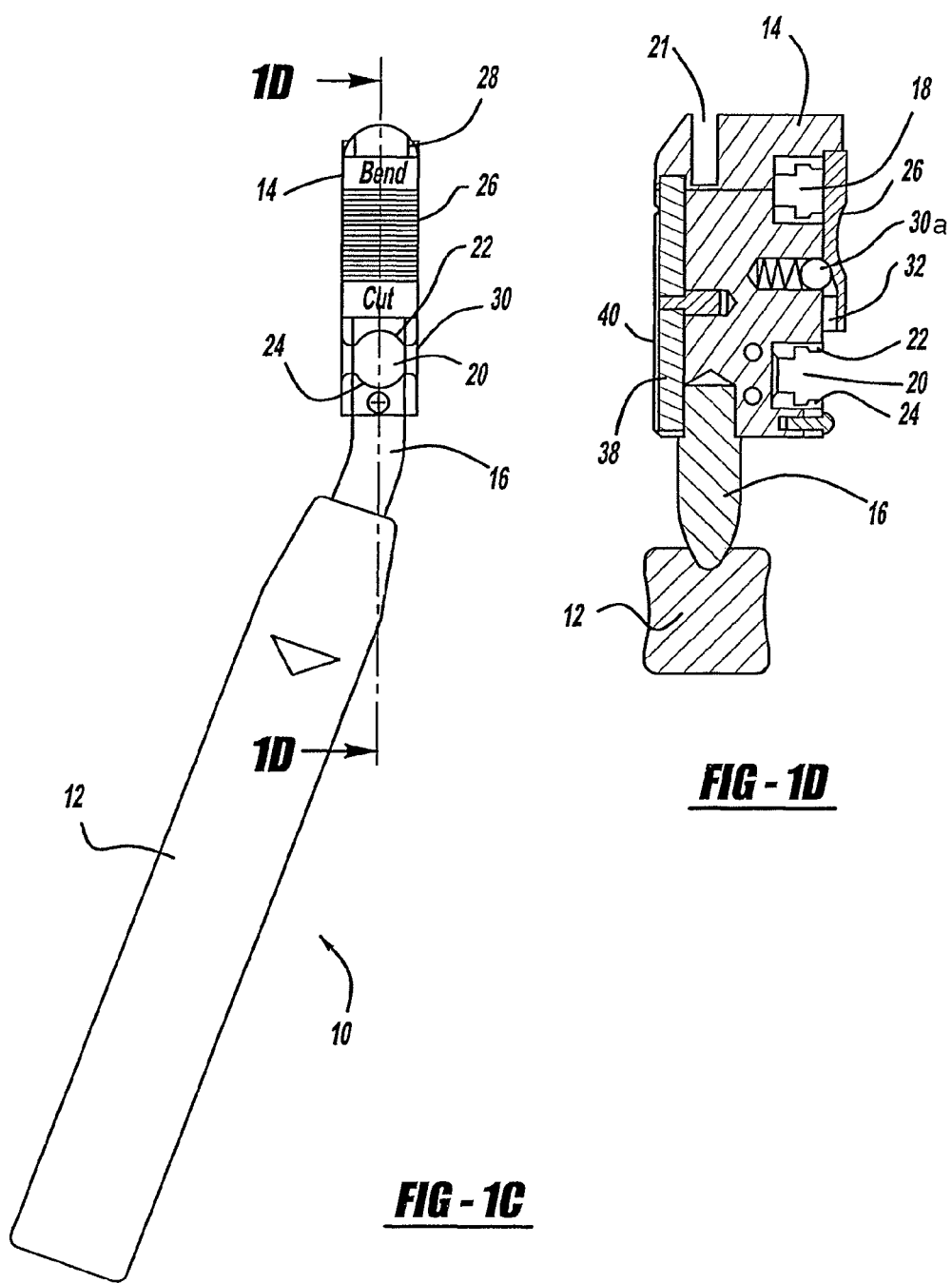

TOOL SYSTEM FOR ADAPTING A BONE PLATE

CROSS-REFERENCE TO RELATED APPLICATION

The instant application is a divisional of, and claims priority to, U.S. patent application Ser. No. 10/446,972, pending, filed May 28, 2003, the entire specification of which is expressly incorporated herein by reference.

FIELD OF THE INVENTION

The invention relates to a tool system for adapting a bone plate to anatomical conditions. More specifically, the invention relates to a tool system having a first tool and a second tool which is used to work on the bone plate at the same time as the first tool.

BACKGROUND OF THE INVENTION

In surgical operations such as reconstructions in the region of the lower jaw, implant systems including bone plates are frequently used. In the context of a surgical operation of this kind, it is frequently necessary to adapt the bone plate to certain anatomical conditions. Adaptations of this kind include, for example, bending and shortening the bone plate.

Bending a bone plate may be performed by means of two clamping pincers. In this case, the clamping pincers are placed at two mutually spaced points on the bone plate and then moved relative to one another. To cut a bone plate, a pincer with cutting jaws is conventionally used.

The object of the invention is to specify an easily handled tool system for working on a bone plate.

SUMMARY OF THE INVENTION

According to an embodiment of the invention, a tool system for adapting a bone plate is specified which includes a first tool and a second tool, used at the same time as the first tool to shorten the bone plate. The first tool has a first introduction opening for the bone plate and a first blade associated with the first introduction opening, and the second tool contains a second introduction opening for the bone plate and a second blade associated with the second introduction opening. At least one of the two tools includes a closing element which may be moved to and fro between a first position allowing the bone plate to be introduced into the respective introduction opening and a second position in which the bone plate is held in the respective introduction opening such that it cannot come free.

According to a further embodiment of the invention, a tool system for adapting a bone plate is proposed which includes a first tool having a first and a second introduction opening for bone plates, and a second tool, used at the same time as the first tool to shorten or bend the bone plate. The second tool is provided with at least a third introduction opening for the bone plate. As regards the first tool, associated with the first introduction opening is a first blade, whereas no blade is associated with the second introduction opening. Associated with the first introduction opening and the second introduction opening is at least one closing element which, in a cutting position, ensures that a bone plate is received in the first introduction opening such that it cannot come free and, in a bending position, makes it possible to receive a bone plate in the second introduction opening such that it cannot come free. The first and the second introduction openings may have a common closing element. It is also possible to provide a first closing element for the first introduction opening and a separate second closing element for the second introduction opening.

According to a further embodiment of the invention, a tool system for adapting bone plates is provided which includes a first tool having a first and a second introduction opening for bone plates, and a second tool having a third and a fourth introduction opening for bone plates. Associated with the first introduction opening and the third introduction opening is in each case at least one blade, whereas no blade is associated in each case with the second introduction opening or the third introduction opening. For cutting the bone plate, the bone plate is arranged in the first and third introduction openings, and for bending it is arranged in the second and fourth introduction openings. One or more of the introduction openings may be of closable construction in order to enable a bone plate which is to be worked on to be received such that it cannot come free. The two tools are used at the same time when shortening or bending the bone plate.

In the described embodiments of the invention, it is possible for a blade to be precisely associated with a particular introduction opening. However, it is also possible for two or more blades to be associated with a particular introduction opening. The blade associated with an introduction opening may delimit the introduction opening in certain sections and, for example, be part of the introduction opening. Additionally or as an alternative thereto, it is possible for a blade which allows closing of the introduction opening to be provided. Thus, it is conceivable for a blade to be constructed on that section of the closing element which is provided for closing a particular introduction opening. If two blades are associated with a particular introduction opening, the first blade may be part of the introduction opening and the second blade may be mounted at a section of the closing element provided for closing this introduction opening.

As regards the shaping of the individual introduction openings, various possibilities are available. For example, an individual or a plurality of introduction openings of a particular tool system may be constructed as a slot-shaped recess in a tool or as a receiving pocket. One or more of the introduction openings may make it possible for the bone plate to be received form-fittingly. This may mean, for example with an introduction opening shaped as a pocket, that the contours of the pocket are adapted to the contours of the bone plate to be worked on.

BRIEF DESCRIPTION OF THE DRAWINGS

Further advantages and details of the invention will become apparent from the description below of a preferred embodiment, and from the figures, in which:

FIG. 1A shows a perspective view of a first tool of a tool system according to the invention;

FIG. 1B shows a side view of the tool according to FIG. 1A;

FIG. 1C shows a plan view of the tool according to FIG. 1A;

FIG. 1D shows a section along the line A-A in FIG. 1C;

FIG. 1E shows a diagrammatic illustration of the cutting functionality of the tool according to FIG. 1A;

DESCRIPTION OF A PREFERRED EMBODIMENT

Figure 2D:
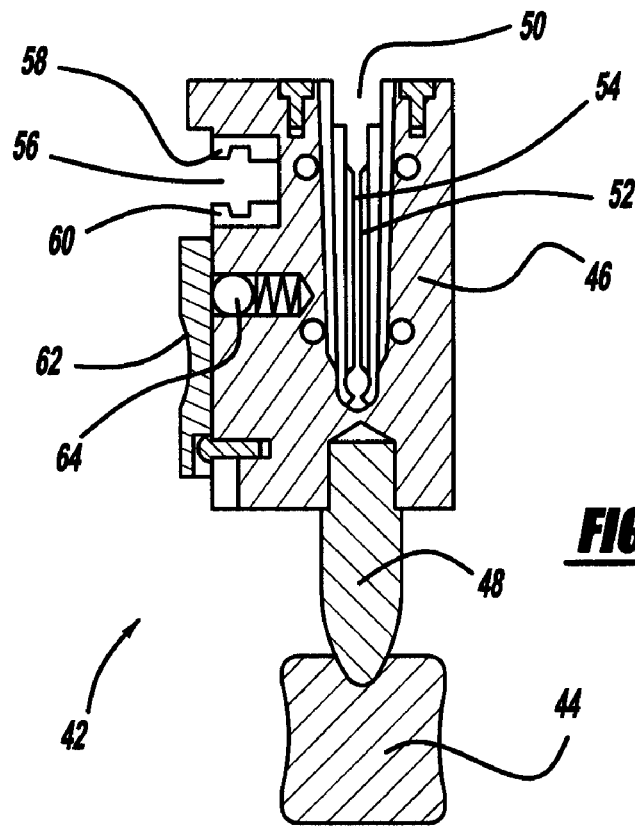
FIG. 2D shows a section along the line A-A in FIG. 2B.
Figure 2A:
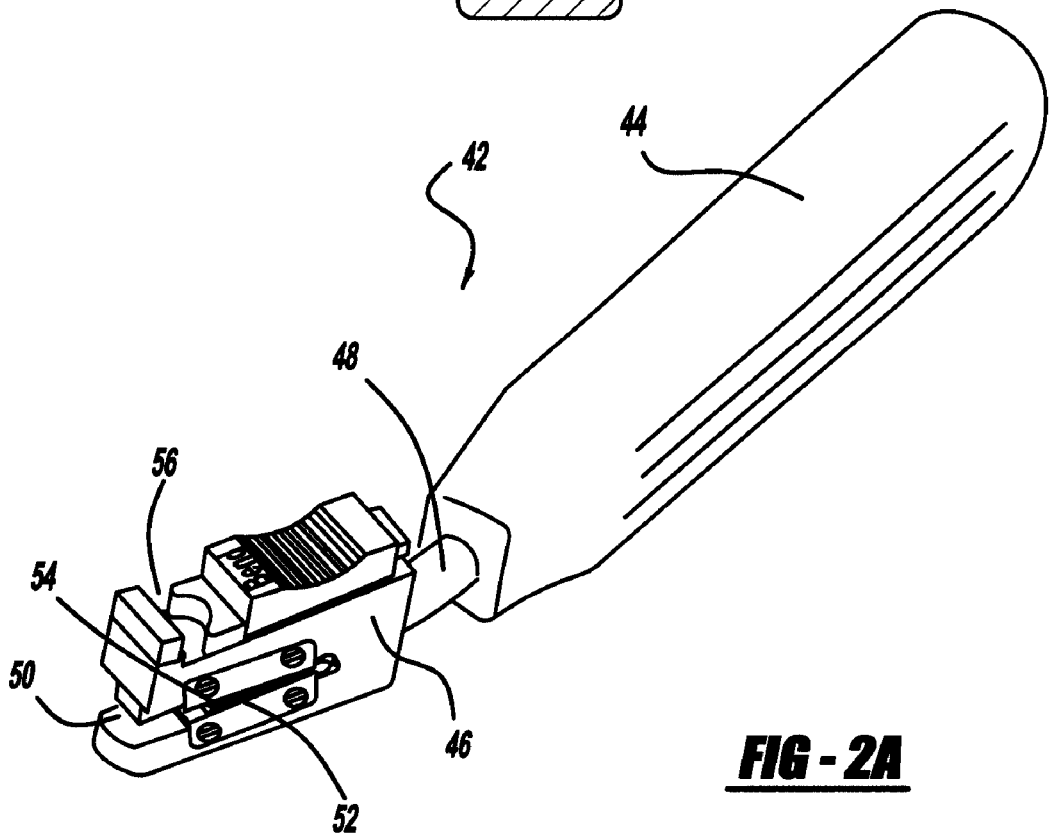
FIG. 2A shows a perspective view of a second tool of the tool system according to the invention.
Figure 2B:
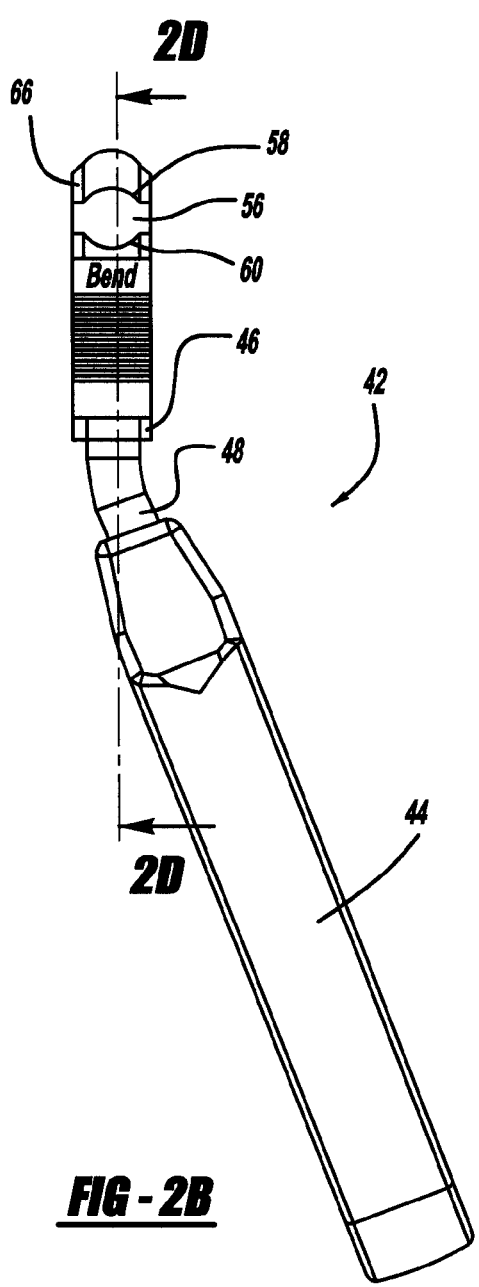
FIG. 2B shows a plan view of the tool according to FIG. 2A.
Figure 2C:
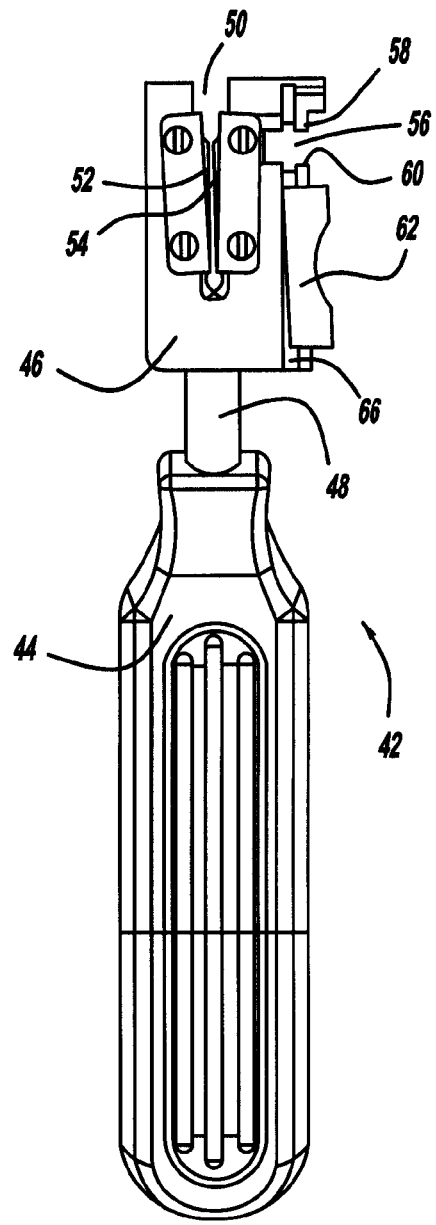
FIG. 2C shows a side view of the tool according to FIG. 2A.

The invention will be explained below by way of example, with reference to a multi-functional tool system. The tool system includes two individual tools which make it possible to both cut and bend a bone plate. However, it is also conceivable to implement the invention with a tool system which has only one of these two functionalities.

To distinguish between them, the two tools of the tool system according to the invention will be designated below on the one hand as the left-hand tool and on the other as the right-hand tool. The terms left and right refer to the fact that the one tool for working on a bone plate is held in the left hand and the other tool is held in the right hand.

In FIGS. 1A to 1E, the left-hand tool 10 of the tool system according to the invention and its mode of operation are illustrated.

The left-hand tool 10 has a tool handle 12 and a tool head 14 which is connected to the handle 12 by means of an angled connection member 16. The handle 12 therefore extends obliquely with respect to the tool head 14. This state of affairs is visible in particular in FIG. 1C. As will be explained below, the angled position of the handle 12 in relation to the tool head 14 makes particularly ergonomic handling of the tool system possible.

Made in the region of the tool head 14 are three introduction openings 18, 20, 21 for bone plates.

The first introduction opening 18 of the left-hand tool 10 is arranged on the upper side of the tool head 14. This can be seen particularly clearly from FIG. 3A. The introduction opening 18 is in the form of a pocket and enables a bone plate which is to be worked on to be received form-fittingly. To this end, the contour of the introduction opening 18 follows the contour of a bone plate to be worked on, and is delimited by two mutually spaced arcuate segments (not designated by reference numerals).

The second introduction opening 20 of the left-hand tool 10 is also arranged on the upper side of the tool head 14. The introduction opening 20 is in the form of a pocket for form-fittingly receiving a bone plate to be worked on. To this end, the contour of the introduction opening 20 follows the contour of a bone plate to be worked on. To be more precise, the introduction opening 20 is delimited by two mutually spaced arcuate segments 22, 24.

The third introduction opening 21 is a slot-shaped recess with no blades, at the front end of the tool head 14. A bone plate to be worked on is introduced into the introduction opening 21 from the front side of the tool head 14 in the direction of the handle 12. The height of the introduction opening 21 corresponds approximately to the overall height of a bone plate to be worked on. The introduction opening 21 may for example be used for bending, as a receiver for a bone plate to be bent.

The left-hand tool 10 illustrated in FIGS. 1A to 1E has a movable closing element 26 provided in the region of the tool head 14, in the form of a sliding unit. The closing element 26 constructed on the upper side of the tool head 14 is movable to and fro along the tool head 14 between two extreme positions. In the position illustrated in FIGS. 1A to 1D, the introduction opening 18 remote from the handle 12 is closed by the closing element 26, and the introduction opening 20 towards the handle 12 is opened for a bone plate to be introduced. If the closing element is moved out of the position illustrated in FIGS. 1A to 1D in the direction of the handle 12, the introduction opening 18 remote from the handle 12 is exposed, and at the same time the introduction opening 20 towards the handle 12 is closed and a bone plate received in the introduction opening 20 is held in this introduction opening 20 such that it cannot come free. This corresponds to the position of the closing element 26 illustrated in FIGS. 1E and 3A. Instead of a single closing element 26, a separate closing element could be provided for each of the two introduction openings 18, 20. It is also conceivable to construct the closing element not as a sliding unit but for example as a rotary or pivotal element in the manner of a bracket or rocker switch.

As visible in FIG. 1B, the closing element 26 engages in a guide groove 28. The guide groove 28 makes it possible to displace the closing element 26 in guided manner along the tool head 14. The closing element 26 is located in a latched position in each of its two extreme positions. To this end, a ball and spring mechanism 30a illustrated in FIG. 1D is provided, which cooperates with two mutually spaced recesses (not indicated in FIG. 1D) on the underside of the closing element 26.

Associated with that introduction opening 20 of the left-hand tool 10 towards the handle 12 are a total of two blades 30, 32. The first blade 30 is part of the introduction opening 20 and the second blade 32 is constructed on the underside of the closing element 26, facing the tool head 14. To be more precise, the first blade 30 is provided in the region of the bottom of the introduction opening 20, and the second blade 26 is provided on a section of the closing element 26 closing the introduction opening 20. By contrast, no blade is associated with the introduction opening 18 remote from the handle 12. In this case, that means that neither the introduction opening 18 itself nor the section of the closing element 26 associated with this introduction opening 18 is provided with a blade.

FIG. 1E shows diagrammatically how the two blades 30, 32 associated with the introduction opening 20 cooperate when a bone plate 36 is being worked on. It is clearly visible that the two blades 30, 32 extend obliquely with respect to one another. This oblique extent of the blades 30, 32 makes it easier to work on cutting the bone plate 36. In conjunction with FIG. 1E, it should be noted that the bone plate 36 may be held clamped between the two blades 30, 32.

A device 38 for deburring a bone plate which has been shortened by means of the tool system according to the invention is constructed on the underside of the tool head 14. The device 38 includes a rough surface 40 coated with diamond.

Referring now to FIGS. 2A to 2D, a right-hand tool 42 of the tool system according to the invention will be explained. Like the left-hand tool, the right-hand tool 42 also includes a tool handle 44 and a tool head 46 which is connected to the handle 44 by means of an angled connection member 48.

The tool head 46 has at its front end remote from the handle 44 an introduction opening 50 for a bone plate. The introduction opening 50 is in the form of a slot-shaped recess which is delimited by two blades 52, 54 extending in a V shape with respect to one another.

On the upper side of the tool head 46 there is a further introduction opening 56 for a bone plate. The introduction opening 56 takes the form of a pocket and corresponds in function and structure to the introduction opening 18 of the left-hand tool 10 illustrated in FIGS. 1A to 1D. Thus, the introduction opening 56 also allows the bone plate that is to be worked on to be received form-fittingly. To this end, two spaced delimiting elements 58, 60 are provided with an arcuate contour.

For the purpose of selectively closing the introduction opening 56, a closing element 62 in the form of a sliding unit is provided on the upper side of the tool head 46. The sliding unit 62 may be moved to and fro between two extreme positions. In the position illustrated in FIGS. 2A to 2D, the sliding unit 62 exposes the introduction opening 56, in other words it allows a bone plate that is to be worked on to be introduced into the introduction opening 56. The sliding unit 62 can be moved out of the position illustrated in FIGS. 2A to 2D into a latched position closing the introduction opening 56. This latched position is illustrated for example in FIGS. 3A and 3C. In its latched position, a bone plate laid in the introduction opening 56 is held form-fittingly in the introduction opening 56 such that it cannot come free. In contrast to the slot-shaped introduction opening 50, no blade is associated with the pocket-shaped introduction opening 56. In this case, that means that neither the introduction opening 56 itself nor the section of the closing element 62 associated with this introduction opening 56 is provided with a blade.

Figure 3A:
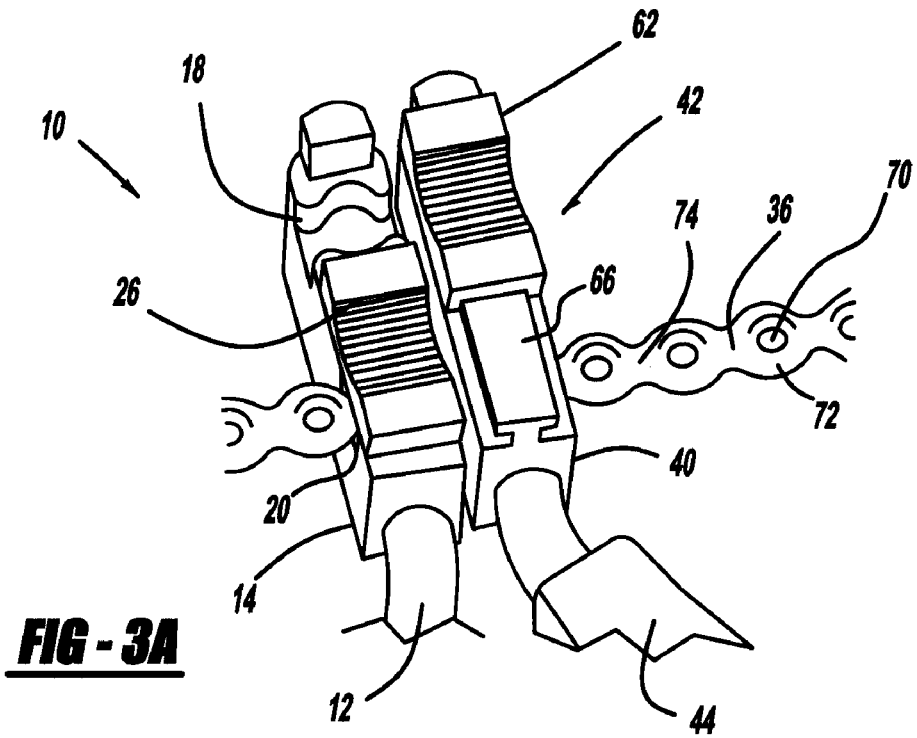
FIG. 3A shows the position of the two tools during cutting work on a bone plate.
Figure 3B:
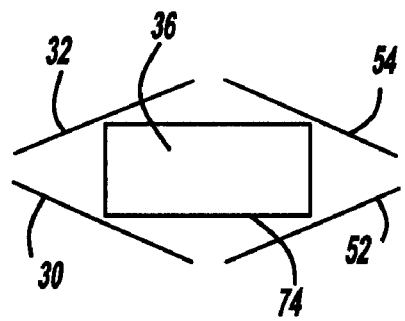
FIG. 3B shows a diagrammatic illustration of the arrangement of the individual blades according to FIG. 3A.
Figure 3C:
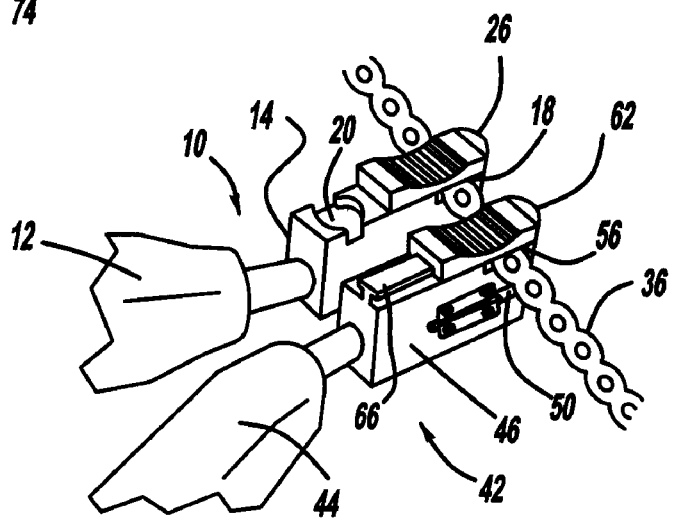
FIG. 3C shows the position of the two tools during bending work on a bone plate.

As is visible from FIG. 2D, a ball and spring mechanism 64 is provided in the tool head 46 and, in a position of the closing element 62 illustrated in FIGS. 3A and 3C, cooperates in latching manner with a recess (not illustrated in the figures) made in the underside of the closing element 62. The closing element 62 engages in a guide groove 66 made in the tool head 46. The guide groove 66 makes it possible to displace the closing element 62 along the tool head 46 in guided manner.

Referring now to FIGS. 3A to 3C, the way the two tools 10, 42 cooperate in order to work on the bone plate 36 will be described.

As shown in FIGS. 3A and 3C, the bone plate 36 is a linear bone plate having a plurality of through openings 70 for securing elements such as bone screws. Laterally, the bone plate 36 has an undulating external contour. The pocket-shaped introduction openings 18, 20, 56 of the tools 10, 42, described with reference to FIGS. 1A to 2D, are constructed, as already mentioned, for the purpose of form-fittingly receiving the bone plate 36. To this end, the delimitations 22, 24, 58, 60, in the shape of circular segments, of the introduction openings 18, 20, 56 are matched to the shape of the bulges 72 on the bone plate 36 in the region of the through openings 70.

In FIGS. 3A and 3B, the way the bone plate 36 is shortened by means of the two tools 10, 42 is illustrated. To this end, the bone plate 36 is first laid form-fittingly in the introduction opening 20, which is equipped with the blade 30 and exposed by the closing element 26, of the left-hand tool 10. Then the closing element 26 is moved out of its position illustrated in FIGS. 1A to 1D, in which it exposes the introduction opening 20, into the position according to FIG. 3A. In this position of the closing element 26, the introduction opening 20 is completely closed and the bone plate 36 is clamped between the blade 30 of the introduction opening 20 on the one hand and the blade 32 of the closing element 26 on the other (see FIG. 3B).

Then the right-hand tool 42 is pushed over the bone plate 36 and at the same time the bone plate 36 is introduced into the introduction opening 50 of the right-hand tool 42, which is equipped with the blades 52, 54. Care is taken to ensure that the tool head 46 of the right-hand tool 42 abuts as closely as possible against the adjoining tool head 14 of the left-hand tool 10. The side wall, on the right in FIG. 3A, of the tool head 14 of the left-hand tool 10 can to this extent serve as a guide face for pushing the tool head 46 of the right-hand tool 42 onto the bone plate 36. Advantageously, the two tools 10, 42 are pushed onto the bone plate 36 in the region of a neck 74 constructed between two adjoining through openings 70.

In the position of the two tools 10, 42 illustrated in FIG. 3A, the bone plate 36 is surrounded by the blades, which are four in total, 30, 32, 52, 54 in the region of a neck 74, as indicated diagrammatically in FIG. 3B. It is clearly visible that each individual one of the blades 30, 32, 52, 54 extends obliquely to each of the other is blades 30, 32, 52, 54.

In order to shorten the bone plate 36, the two tools 10, 42 are moved in rotation relative to one another, with the bone plate 36 approximately indicating the common axis of rotation of the two tools 10, 42. From an ergonomic point of view, it is advantageous that the two tool handles 12, 44 extend obliquely with respect to one another, since this makes handling of the two tools 10, 42 easier when the bone plate 36 is cut.

Following shortening of the bone plate 36 by means of the two tools 10, 42, the shortened bone plate 36 may be deburred. To this end, the shortened end of the bone plate 36 is worked on by means of the diamond-coated surface 40 on the underside of the tool head 14.

Referring now to FIG. 3C, bending of the bone plate 36 will be explained. To bend the bone plate 36, the bone plate 36 is first laid in the introduction opening 18 of the left-hand tool 10, exposed by the closing element 26. Then the bone plate 36, which is arranged form-fittingly in the introduction opening 18, is held in the introduction opening 18 in a position in which the introduction opening 18 is closed (with the bone plate 36 received therein) by a displacement of the closing element 26, such that it cannot come free.

Following this, the bone plate is introduced into the introduction opening 56 of the right-hand tool 42, which is exposed by the closing element 62. Thereupon the closing element 62 is moved into a position closing the introduction opening 58, with the bone plate 36 received therein. The bone plate 36 is now held form-fittingly and such that it cannot come free, both in the introduction opening 18 of the left-hand tool 10 and in the introduction opening 56 of the right-hand tool 42. When the bone plate 36 is introduced into the introduction opening 56 of the right-hand tool 42, care is taken to ensure that a certain spacing is maintained between the two tool heads 14, 46. This spacing is necessary to make bending the bone plate 36 possible by means of a suitable relative movement between the two tools 10, 42. The tools 10, 42 can be used to bend the bone plate 36 both within the plane established by the bone plate 36 and out of this plane.

The invention claimed is:

1. A tool system for adapting a bone plate, including
a first tool having a first and a second introduction opening for bone plates, wherein a first blade is associated with the first introduction opening, no blade is associated with the second introduction opening, and there being associated with the first introduction opening and the second introduction opening at least one closing element which, in a cutting position, ensures that a bone plate is received in the first introduction opening such that it cannot come free and, in a bending position, makes it possible to receive a bone plate in the second introduction opening such that it cannot come free; and
a second tool, used at the same time as the first tool to shorten or bend the bone plate, with the second tool being provided with at least a third introduction opening for the bone plate.

2. A system according to claim 1, wherein the closing element is common to the first and second introduction openings and, in the cutting position of the closing element, the second introduction opening is exposed for the bone plate to be introduced and, in the bending position, the first introduction opening is exposed for the bone plate to be introduced.

3. A system according to claim 1, wherein the closing element is a sliding unit.

4. A system according to claim 1, wherein a section of the closing element constructed to close the first introduction opening is provided with the first blade.

5. A system according to claim 1, wherein the first introduction opening and the second introduction opening are in the form of pockets for receiving the bone plate, and wherein each of the pockets is closable by the closing element.

6. A system according to claim 1, wherein at least one of the two introduction openings allows the bone plate to be received form-fittingly.

7. A system according to claim 1, wherein the third introduction opening is a recess in the second tool, provided with at least a second blade.

8. A system according to claim 7, wherein the second tool has a fourth introduction opening.

9. A system according to claim 8, wherein, for the purpose of closing the fourth introduction opening, a further closing element is provided which, in a first position, allows the bone plate to be introduced into the fourth introduction opening and, in a second position, enables the bone plate to be received in the fourth introduction opening such that it cannot come free.

10. A system according to claim 8, wherein the fourth introduction opening is constructed with no blades and allows the bone plate to be received form-fittingly.

11. A tool system for adapting bone plates, including
a first tool having a first and a second introduction opening for bone plates, with at least one blade being associated with the first introduction opening and no blade being associated with the second introduction opening, and
a second tool, used at the same time as the first tool to shorten or bend the bone plate, with the second tool being provided with a third and a fourth introduction opening, with at least one blade being associated with the third introduction opening and the fourth introduction opening being constructed with no blades, and, for cutting, the bone plate being arranged in the first and third introduction openings and, for bending, the bone plate being arranged in the second and fourth introduction openings
wherein at least one of the two tools includes a movable closing element which, in a cutting position, closes at least one of the first introduction opening and the third introduction opening and, in a bending position, closes at least one of the second introduction opening and the fourth introduction opening.

12. A system according to claim 11, wherein the first and the second tools each include a tool head and a tool handle, and wherein the introduction opening is in each case constructed in the region of the tool head.

13. A system according to claim 12, wherein the tool handle of at least one of the two tools extends at an angle with respect to the tool head.

14. A system according to claim 11, furthermore including an elongate bone plate having an undulating lateral contour and having a plurality of through openings for securing elements.

* * * * *